United States Patent

Neef et al.

Patent Number: 5,411,949
Date of Patent: May 2, 1995

[54] 23-OXA-DERIVATIVES IN THE VITAMIN D SERIES, PROCESS FOR THEIR PRODUCTION, PHARMACEUTICAL PREPARATIONS CONTAINING THESE DERIVATIVES AS WELL AS THEIR USE PHARMACEUTICAL AGENTS

[75] Inventors: Günter Neef; Andreas Steinmeyer; Gerald Kirsch; Katica Schwarz; Martin Haberey; Ruth Thieroff-Ekerdt; Petra Rach, all of Berlin, Germany

[73] Assignee: Schering Aktiengesellschaft, Berlin and Bergkamen, Germany

[21] Appl. No.: 90,201

[22] PCT Filed: Jan. 20, 1992

[86] PCT No.: PCT/EP92/00123
§ 371 Date: Jul. 19, 1993
§ 102(e) Date: Jul. 19, 1993

[87] PCT Pub. No.: WO92/12963
PCT Pub. Date: Aug. 6, 1992

[30] Foreign Application Priority Data
Jan. 19, 1991 [DE] Germany .......... 41 01 953.9

[51] Int. Cl.⁶ .......................................... C07C 401/00
[52] U.S. Cl. ................................. 514/167; 552/653
[58] Field of Search ..................... 552/653; 514/167

[56] References Cited

FOREIGN PATENT DOCUMENTS
9115475 10/1991 WIPO .......... C07C 401/00

OTHER PUBLICATIONS
Kubodera, et al., Chem. Pharm. Bull., 39(12), 1991, pp. 3221-3224.

Primary Examiner—Johann Richter
Assistant Examiner—Kimberly J. Kestler
Attorney, Agent, or Firm—Millen, White, Zelano, & Branigan

[57] ABSTRACT

23-Oxa-derivatives in the vitamin D series of formula I

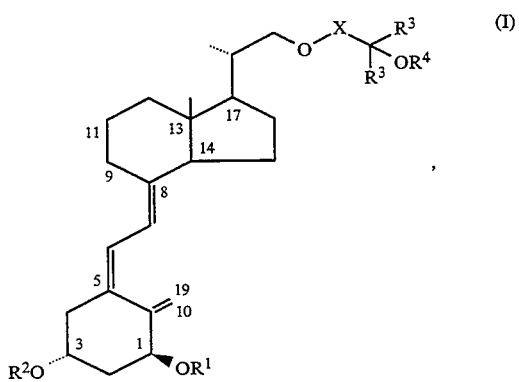

are described in which
 $R^1$, $R^2$ and $R^4$ independently of one another mean a hydrogen atom or an acyl group with 1 to 9 carbon atoms,
 $R^3$ each means a hydrogen atom or each a linear or branched alkyl group with 1 to 4 carbon atoms and X means an alkylene radical—$(CH_2)_n$— with $n=1$, 2, 3, and if $n=1$, $R^3$ each cannot be a methyl or propyl group, as well as a process for their production.

The compounds have proliferation-inhibiting and cell-differentiation effects and are suitable for the production of pharmaceutical agents.

5 Claims, No Drawings

23-OXA-DERIVATIVES IN THE VITAMIN D SERIES, PROCESS FOR THEIR PRODUCTION, PHARMACEUTICAL PREPARATIONS CONTAINING THESE DERIVATIVES AS WELL AS THEIR USE PHARMACEUTICAL AGENTS

This invention relates to 23-oxa-derivatives in the vitamin D series of formula I

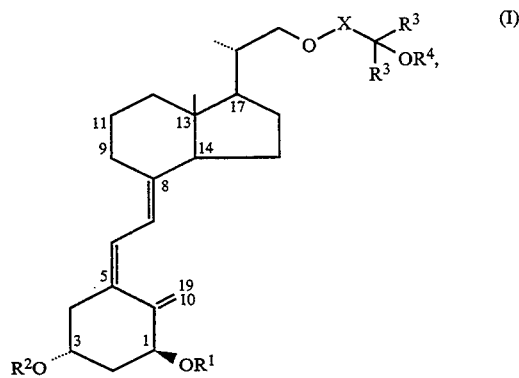

in which
R$^1$, R$^2$ and R$^4$ independently of one another mean a hydrogen atom or an acyl group with 1 to 9 carbon atoms,
R$^3$ each means a hydrogen atom or each a linear or branched alkyl group with 1 to 4 carbon atoms and X means an alkylene radical —(CH$_2$)$_n$— with n=1, 2, 3, and if n=1, R$^3$ each cannot be a methyl or propyl group, as well as a process for their production, pharmaceutical preparations that contain these compounds as well as their use for the production of pharmaceutical agents.

The acyl groups possible for radicals R$^1$, R$^2$ and R$^4$ are derived especially from saturated or even unsaturated, straight-chain or branched carboxylic acids or benzoic acid.

As alkyl groups for R$^3$ methyl, ethyl or propyl groups are first of all suitable.

Preferred, according to this invention, are 23-oxa-vitamin D derivatives of general formula I, in which R$^1$, R$^2$ and R$^4$ stand for a hydrogen atom and R$^3$ each stands for an ethyl group.

Especially preferred are the compounds
24-(1-ethyl-1-hydroxypropyl)-23-oxa-9,10-seco-5(Z),7(E),10(19)-cholatriene-1α,3β-diol,
24-(1-hydroxy-1-propylbutyl)-23-oxa-9,10-seco-5(Z),7(E),10(19)-cholatriene-1α,3β-diol,
24-(3-hydroxy-3-methylbutyl)-23-oxa-9,10-seco-5(Z),7(E),10(19)-cholatriene-1α,3β-diol,
24-(3-ethyl-3-hydroxypentyl)-23-oxa-9,10-seco-5(Z),7(E),10(19)-cholatriene-1α,3β-diol.

Vitamin D derivatives that can be substituted in 1 and 3 position as the compounds according to the invention and the side chain

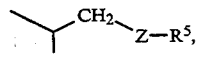

in which Z, i.a., stands for an oxygen atom and R$^5$ for a straight-chain or branched-chain, optionally substituted aliphatic group with 1 to 12 carbon atoms, are described in EP-A-0078 704. Especially preferred here are the compounds in which Z, i.a., means an oxygen atom and R$^5$ means the group —CH$_2$—C(CH$_3$)$_2$OR$^6$ (R$^6$=H, hydroxy protective group).

Natural vitamins D$_2$ and D$_3$ (cf. general formula VIII) are in themselves biologically inactive and are converted not until after hydroxylation in 25 position in the liver or in 1 position in the kidneys into their biologically active metabolites. The effect of vitamins D$_2$ and D$_3$ consists in the stabilization of the plasma-Ca$^{++}$ level and plasma phosphate level; they counteract a drop of the plasma-Ca$^{++}$ level.

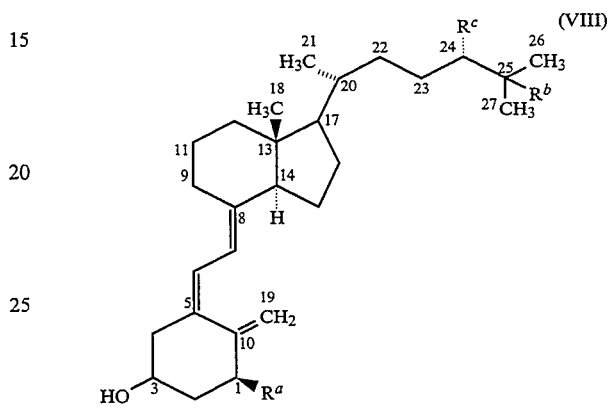

Ergocalciferol: R$^a$ = R$^b$ = H, R$^c$ = CH$_3$, Doppelbindung C-22/23   Vitamin D$_2$
Cholecalciferol: R$^a$ = R$^b$ = R$^c$ = H   Vitamin D$_3$
25-Hydroxycholecalciferol: R$^a$ = R$^c$ = H, R$^b$ = OH
1α-Hydroxycholecalciferol: R$^a$ = OH, R$^b$ = R$^c$ = H
1α,25-Dihydroxycholecalciferol:   Calcitriol
R$^a$ = R$^b$ = OH, R$^c$ = H In addition to their pronounced effect on the calcium and phosphate metabolism, vitamins D$_2$ and D$_3$ and their synthetic derivatives also have proliferation-inhibiting and cell-differentiating effects (H. F. De Luca, The Metabolism and Function of Vitamin D in Biochemistry of Steroid Hormones, Editor H. L. J. Makin, 2nd Edition, Blackwell Scientific Publications 1984, pp 71–116). However in vitamin D use it is possible to have overdose symptoms (hypercalcemia).

In 24 position hydroxylated 1α-cholecalciferols are already known from DE-AS 25 26 981; they have less toxicity than the corresponding nonhydroxylated 1α-cholecalciferol. The hydroxylated compounds show a selective activation of intestinal calcium absorption and a weaker bone absorption effect than 1α-cholecalciferol.

The 24-hydroxy-vitamin D analogs described in international patent application WO 87/00834 can be used for the treatment of disorders caused by abnormal cell proliferation and/or cell differentiation in humans and animals.

For various 1,25-dihydroxy-homo-vitamin D derivatives a dissociation relative to the properties bone absorption effect and HL-60 cell differentiation recently has been mentioned by De Luca. The bone absorption effect in vitro here is a direct measurement for the calcium mobilization in vivo.

It has now been found that the 23-oxa-vitamin D derivatives of general formula I according to the invention in comparison with vitamin D derivative calcitriol (1α,25-dihydroxycholecalciferol) surprisingly have a more favorable spectrum of activity. While the effects on the calcium and phosphate metabolism are markedly weakened (reduction of the side effects by overdosage or necessary high dosage), the proliferation-inhibiting and cell-differentiating effects are approximately retained (dissociation).

The vitamin D activity of the compounds according to the invention is determined by the calcitriol receptor test. It is performed by using a specific receptor protein from the intestine of young pigs (see Dame, M. C.; Pierce, E. A.; DeLuca, H. F.; *Proc. Natl. Acad. Sci. USA*, 82, 7825 (1985)). A receptor-containing binding protein is incubated with an ethanolic solution of $^3$H-calcitriol (0.025 μCi) in a reaction volume of 0.25 ml in absence and in presence of the test substances for two hours in a test tube. A charcoal-dextran absorption is performed for the separation of free and receptor-bound calcitriol. For this purpose 250 μl of a charcoal-dextran suspension is fed to each test tube and incubated at 4° C. for 20 minutes. Then the samples are centrifuged at 1500×g 10 minutes at 4° C. The supernatant is decanted and measured after about 1 hour equilibration in atomic light in a β-counter.

The competition curves resulting with various concentrations of test substance as well as of the reference substance (unlabeled calcitriol) at constant concentration of reference substance ($^3$H-calcitriol) are placed in relation to one another and a competition factor (KF) is determined.

It is defined as quotient from the concentrations of the respective test substance and the reference substance, that are necessary for 50% competition:

$$KF = \frac{\text{Concentration of test substance at 50\% competition}}{\text{Concentration of reference substance at 50\% competition}}$$

Accordingly
24-(1-ethyl-1-hydroxypropyl)-23-oxa-9,10-seco-5(Z),7(E),10(19)-cholatriene-1α,3β-diol (6a),
24-(1-hydroxy-1-propylbutyl)-23-oxa-9,10-seco-5(Z),7(E),10(19)-cholatriene-1α,3β-diol (6b) and
24-(3-hydroxy-1-methylethyl)-23-oxa-9,10-seco-5(Z),7(E),10(19)-cholatriene-1α,3β-diol (6c) have KF-values of 2.2 (6a), 4.5 (6b) and 4.6 (6c).

These data show that the described compounds bind with about the same strength as calcitriol to the latter's receptor.

The compounds according to the invention show a significant orthokeratosis induction on the tail of a mouse without influencing the Ca$^{2+}$-metabolism.

Comparison compound 6c in an analogous stimulation of the stratum granulosum considerably affects the calcium-metabolism.

The mouse tail physiologically exhibits, besides areas with orthokeratotic hornification, also parakeratotic stratum corneum. By topical application of calcitriol analogs and other substances, such as, e.g., vitamin A acid and the antipsoriatically effective dithranol, an orthokeratotic hornification of the parakeratotic skin can be induced. A measuring parameter is the percentage increase of the part of the epidermis regions that have, in the histological preparation, a stratum granulosum as marker of orthokeratosis. (R. Wrench: Assessing Drugs for Psoriasisform Diseases and their Antiparakeratotic Mechanisms Using the Mouse Tail Test; Maibach, Lowe (eds.) *Models in Dermatology*, vol. 2, pp 76–91 (Karger, Basel 1985)).

At the same time the dissociation between local growth regulating and systemic calcitropic effect is observed in this model by determination of the calcium concentration in the serum

|  | stimulation of stratum granulosum | Ca$^{2+}$ serum |
|---|---|---|
| compound 6b (invention) | 41% | 2.75 mmol/l |
| compound 6c (comparison) | 41% | 3.645 mmol/l |
| solvent control (ethanol/isopropyl myristate) (95/5 V/V) | — | 2.73 mmol/l |

Species: mouse; sex: female; manner of application: topical; application time: 19 days; application volume: 0.05 ml once daily Monday–Friday; formulation: dissolved in ethanol/isopropyl myristate; dosage of the test substance: 0.005%. By the reduced hypercalcemia risk, the substances according to the invention are especially suitable for the production of pharmaceutical agents for the treatment of diseases that are characterized by hyperproliferation, e.g., hyperproliferative diseases of the skin (psoriasis) and malignant tumors (leukemia, colon cancer, breast cancer).

In an especially preferred embodiment of the invention calcitriol receptors are detected before the treatment in the target organ.

Thus this invention also relates to pharmaceutical preparations that contain at least a compound according to general formula I together with a pharmaceutically compatible vehicle. The compounds can be formulated as solutions in pharmaceutically compatible solvents or as emulsions, suspensions or dispersions in suitable pharmaceutical solvents or vehicles or as pills, tablets or capsules, that contain solid vehicles in a way known in the art. For topical use the compounds are preferably formulated as creams or ointments or in a similar pharmaceutical form suitable for topical use. Every such formulation can also contain other pharmaceutically compatible and nontoxic auxiliary agents, such as, e.g. stabilizers, antioxidants, binders, dyes, emulsifiers or flavoring substances. The compounds are advantageously applied by injection or intravenous infusion of suitable sterile solutions or as oral dosage by the digestive tract or topically in the form of creams, ointments, lotions or suitable transdermal plasters, as described in EP-A 0387 077.

The daily dose is
0.1 μg/patient/day—1000 μg (1 mg)/patient/day, preferably
1.0 μg/patient/day—500 μg/patient/day.

Further the invention relates to the use of compounds according to formula I for the production of pharmaceutical agents.

The production of compounds of general formula I', (these are the compounds of general formula I as well as those compounds that are added by the omission of the disclaimer in general formula I) takes place according to a new process.

Therefore the invention also relates to a process for the production of compounds of general formula I'

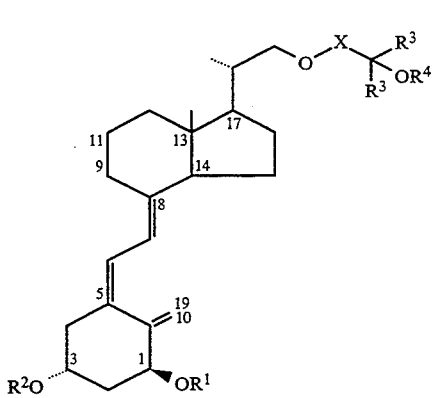

(I')

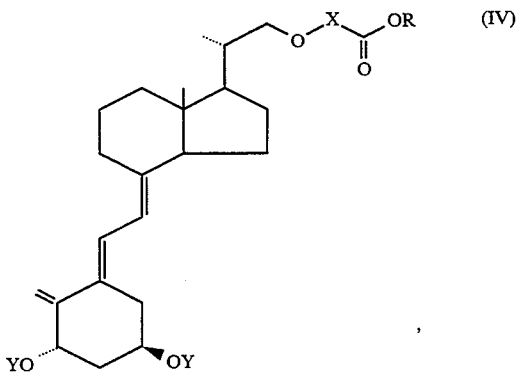

(IV)

in which

R$^1$, R$^2$ and R$^4$ independently of one another mean a hydrogen atom or an acyl group with 1 to 9 carbon atoms, R$^3$ each means a hydrogen atom or each means a linear or branched alkyl group with 1 to 4 carbon atoms and X means an alkylene radical —(CH$_2$)$_n$— with n=1, 2, 3 characterized in that a compound of general formula II

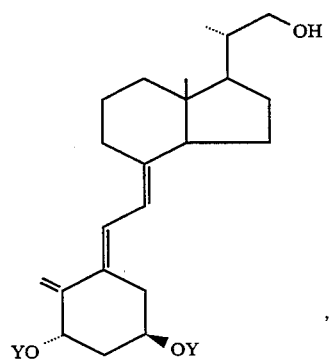

(II)

in which Y means alkyl or aryl substituted silyl groups, is etherified with a compound of general formula III

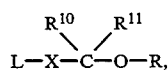

(III)

in which

L stands for a leaving group Br, I, CH$_3$—C$_6$H$_4$SO$_2$O—,

X stands for an alkylene radical —(CH$_2$)$_n$— with n=1, 2 or 3,

R stands for a straight-chain or branched alkyl radical with 1 to 8 carbon atoms as well as R$^{10}$ and R$^{11}$ also each stand for a radical OR or R$^{10}$ and R$^{11}$ together stand for an oxygen atom, thus obtaining a compound of general formula IV on whose carbonyl group a nucleophilic reagent of general formula V is added in which R$^3$ means a linear or branched alkyl group with 1 to 4 carbon atoms and Z MgHal (Hal=Cl, Br, I) or an alkali atom (Li, Na, K)

or if R$^3$ each is to be a hydrogen atom, the carbonyl group is reacted with a complex hydride, such as, for example, lithium aluminum hydride, with the formation of a compound of general formula VI

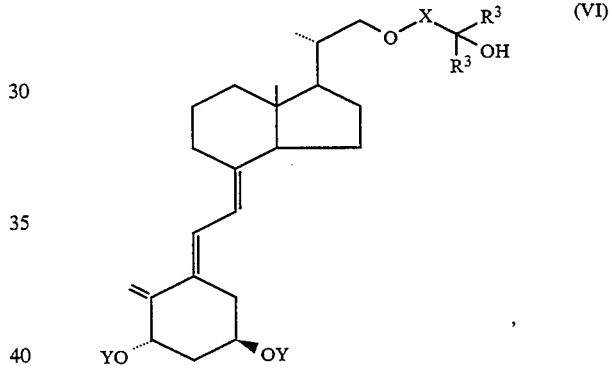

(VI)

and the latter is converted by photochemical isomerization of the triene system in the presence of a triplet sensitizer into a compound of general formula VII

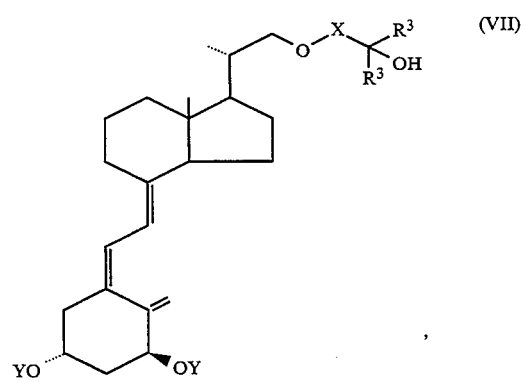

(VII)

and the silyl protective groups are cleaved off and then optionally the free hydroxy groups are partially or completely esterified with a carboxylic acid chloride or anhydride, which have 1 to 9 carbon atoms in the acyl radical.

The addition of nucleophilic reagent of general formula V to the carbonyl group of the compound of general formula IV can be performed according to the invention under phase transfer conditions.

The conversion of a compound of general formula VI into a compound of general formula VII takes place, e.g., by irradiation with ultraviolet light in the presence of a so-called "triplet sensitizor." In the context of this invention anthracene is used for this purpose. The stereoisomerism is reversed by cleavage on the 5,6 double bond of the pi bond of the 5,6 double bond, rotation of the A ring by 180° around the 5,6 single bond and reestablishing the 5,6 double bond.

Then existing hydroxy protective groups are cleaved off, preferably by using tetra-n-butyl-ammonium fluoride and optionally the free hydroxy groups are partially or completely esterified according to common processes with the corresponding carboxylic acid halide (halide=chloride, bromide) or carboxylic acid anhydride.

The following examples provide a more detailed explanation of the invention.

The 20(S)-formyl compound necessary for the production of 20(S)-hydroxymethyl compound 2 is described by M. J. Calverley in *Tetrahedron* 43, p 4609, 1987.

EXAMPLES

1α,3β-Bis[[dimethyl(1,1-dimethylethyl)silyl]oxy]-20(S)hydroxymethyl-9,10-seco-5(E),7(E), 10(19)-pregnatriene 2

4.4 g of 1α,3β-bis[[dimethyl(1,1-dimethylethyl)silyl]oxy]-20 (S)-formyl-9,10-seco-5(E) ,7(E) ,10(19)-pregnatriene is dissolved in 20 ml of ethanol and 2 ml of tetrahydrofuran and mixed at 0° C. with 100 mg of boronhydride. 20 ml of sodium chloride solution is then added after stirring for one hour at room temperature. It is extracted with methylene chloride, dried on sodium sulfate and concentrated by evaporation. 4.4 g of the title compound is obtained as colorless crystals.

$^1$H-NMR (CDCl$_3$): δ=0.01 ppm (s, 12H, Si—CH$_3$); 0.51 (s, 3H, H-18); 0.81 and 0.83 (s; 9H, Si-t-butyl each); 1.01 (d, J=7 Hz, 3H, H-21); 3.36 (m, 1H, H-22); 3.61 (ddbr, J=11.5 Hz, 1H, H-22'); 4.17 (m, 1H, H-3); 4.48 (dd, J=10, 4 Hz, 1H, H-1); 4.89 and 4.93(s; 1H, H-19 each); 5.78 and 6.40 (d, J=11 Hz; 1H, H-6 and H-7 each)

Melting point: 107°–109° C.
[α]$_D^{20}$: +54.2°; c=0.5; CHCl$_3$

1α,3β-Bis[[dimethyl(1,1-dimethylethyl)silyl]oxy]-23-oxa-9,10-seco-5(E),7(E),10(19)-cholatriene-24-carboxylic acid-1,1-dimethylethyl ester 3

2.5 g of compound 2 is dissolved in 50 ml of toluene, 6.3 g of bromoacetic acid-tert.-butyl ester is added and then mixed with 20 ml of 25% sodium hydroxide solution and 93 mg of tetrabutylammonium hydrogen sulfate. It is now stirred for 24 hours at room temperature, 50 mg of the catalyst is again added and stirred for another 6 hours. The mixture is poured on sodium chloride solution, extracted with ethyl acetate, dried on sodium sulfate and concentrated by evaporation. The product is purified chromatographically with hexane/ethyl acetate on silica gel, and 1.375 g of the title compound is obtained as colorless foam.

$^1$H-NMR (CHCl$_3$): δ=0.01 ppm (s, 12H, Si—CH$_3$); 0.50 (s, 3H, H-18); 0.80 and 0.84 (s; 9H, Si-t-butyl each); 1.03 (d, J=7 Hz, 3H, H-21); 1.42 (s, 9H, t-butylester); 3.21 (dd, J=9.75 Hz, 1H, H-22); 3.42 (m, 1H, H-22'); 3.88 (s, 2H, H-24); 4.18 (m, 1H, H-3); 4.49 (m, 1H, H-1); 4.88 and 4.94 (s; 1H, H-19 each); 5.78 and 6.40 (d, J=11 Hz; 1H, H-6 and H-7 each)

1α,3β-Bis[[dimethyl(1,1-dimethylethyl)silyl]oxy]-24-(1-ethyl-hydroxy-propyl)-23-oxa-9,10-seco-5(E),-7(E),10(19)-cholatriene 4a The Grignard reagent is prepared from 0.54 ml of bromoethane and 174 mg of magnesium chips in 5 ml of tetrahydrofuran. 500 mg of compound 3 in 2 ml of tetrahydrofuran is now added at 0° C. and stirred for 1 hour. It is then hydrolyzed with ammonium chloride solution, extracted with ethyl acetate, dried on sodium sulfate and concentrated by evaporation. After chromatography with hexane/ethyl acetate on silica gel, 246 mg of the title compound is obtained as colorless foam.

$^1$H-NMR (CDCl$_3$): δ=0.01 ppm (s, 12H, Si—CH$_3$); 0.50 (s, 3H, H-18); 0.78 and 0.82 (s; 9H, Si-t-butyl each); 0.81 and 0.87 (t, J=7 Hz; 3H, H-28 and H-29 each); 0.98 (d, J=7 Hz, 3H, H-21); 3.13 (dd, J=9.6 Hz, 1H, H-22); 3.14 (d, J=9.5 Hz, 1H, H-24); 3.22 (d, J=9.5 Hz, 1H, H-24'); 3.35 (dd, J=9, 3.5 Hz, 1H, H-22'); 4.15 (m, 1H, H-3); 4.48 (m, 1H, H-1); 4.88 and 4.93 (s; 1H, H-19 each); 5.77 and 6.40 (d, J=11 Hz; 1H, H-6 and H-7 each) [α]$_D^{20}$:+62.3°, c=0.215; CHCl$_3$ 1α,3β-Bis[[dimethyl(1,1-dimethylethyl)silyl]oxy]-24-(1-ethyl-1-hydroxy-propyl)-23-oxa-9,10-seco-5(Z),7(E),10(19)-cholatriene 5a 246 mg of 4a is dissolved together with 35 mg of anthracene and 10 μl of triethylamine in 80 ml of toluene and irradiated 6 minutes in a pyrex immersion reactor by a mercury high-pressure lamp (Philips HPK 125)under a nitrogen atmosphere. After concentration by evaporation the substance is chromatographed on silica gel with hexane/ethyl acetate, and 202 mg of the title compound is obtained as colorless foam.

$^1$H-NMR (CDCl$_3$): δ=0.01 ppm (s, 12H, Si—CH$_3$); 0.50 (s, 3H, H-18); 0.83 (s, 18H, Si-t-butyl); 0.81 and 0.85 (t, J=7 Hz; 3H, H-28 and H-29 each); 0.98 (d, J=7 Hz, 3H, H-21); 3.12 (dd, J=10, 6 Hz, 1H, H-22); 3.13 (d, J=9.5 Hz, 1H, H-24); 3.22 (d, J=9.5 Hz, 1H, H-24'); 3.35 (dd, J=10, 3.5 Hz, 1H, H-22'); 4.13 (m, 1H, H-1); 4.31 (m, 1H, H-1); 4.80 and 5.12 (s; 1H, H-19 each); 5.96 and 6.18 (d, J=11 Hz; 1H, H-6 and H-7 each) [α]$_D^{20}$: +41.3°, c=0.23; CHCl$_3$ 24-(1-Ethyl-1-hydroxypropyl)-23-oxa-9,10-seco-5(Z),7(E),10(19)colatriene-1α,3β-diol 6a 190 mg of 5a is dissolved in 3.5 ml of tetrahydrofuran and mixed with 1.13 ml of tetrabutylammonium fluoride solution (1M in THF). It is stirred for 1 hour at 60° C. The reaction mixture is now stirred for 10 minutes with sodium bicarbonate solution, extracted with ethyl acetate, dried on sodium sulfate and concentrated by evaporation. The product is purified by chromatography on silica gel with hexane/ethyl acetate and 66 mg of the title compound is obtained as colorless foam.

$^1$H-NMR (CDCl$_3$): δ=0.56 ppm (s, 3H, H-18); 0.85 (t, J=7 Hz, 6H, H-28 and H-29); 1.03 (d, J=7 Hz, 3H, H-21); 3.18 (dd, J=9, 5.5 Hz, 1H, H-22); 3.20 (d, J=10 Hz, 1H, H-24); 3.28 (d, J=10 Hz, 1H, H-24'); 3.40 (dd, J=9, 4.5 Hz, 1H, H-22'); 4.24 (m, 1H, H-3); 4.44 (m, 1H, H-1); 5.00 and 5.32 (s; 1H, H-19 each); 6.03 and 6.38 (d, J=11 Hz; 1H, H-6 and H-7 each) [α]$_D^{20}$: +20.3°, c=0.265; CHCl$_3$

1α,3β-Bis[[dimethyl(1,1-dimethylethyl)silyl]oxy]-24-(1-hydroxy-1-propylbutyl)-23-oxa-9,10-seco-5(E),-7(E),10(19)-cholatriene 4b 400 mg of 3 is reacted with the Grignard reagent prepared from 140 mg of magnesium chips and 0.52 ml of 1-bromopropane analogous to 4a. 160 mg of the title compound is obtained as colorless foam.

$^1$H-NMR (CHCl$_3$): δ=0.01 ppm (s, 12H, Si—CH$_3$); 0.50 (s, 3H, H-18); 0.80 and 0.85 (s; 9H, Si-t-butyl each); 0.81 and 0.83 (t, J=7 Hz, 6H, H-30 and H-31); 0.99 (d, J=7 Hz, 3H, H-21); 3.08 (dd, J=9, 7.5 Hz, 1H, H-22); 3.35 (m, 3H, H-22′ and H-24); 4.18 (m, 1H, H-3); 4.49 (m, 1H, H-1); 4.88 and 4.94 (m, 1H, H-19); 5.78 and 6.40 (d, J=11 Hz; 1H; H-6 and H-7 each) [α]$_D^{20}$: +55.2°, c=0.46; CHCl$_3$

1α,3β-Bis[[dimethyl(1,1-dimethylethyl)silyl]oxy]-24-(1-hydroxy-1propylbutyl)-23-oxa-9,10-seco-5(Z),7(E), 10(19)-cholatriene 5b 150 mg of 4b is reacted with 20 mg of anthracene and 5.8 ∞l of triethylamine analogous to 5a, and 125 mg of the title compound is obtained as colorless foam.

$^1$H-NMR (CDCl$_3$): δ=0.01 ppm (s, 6H, Si—CH$_3$); 0.49 (s, 3H, H-18); 0.80 (s, 18H, Si-t-butyl); 0.80 (t, J=7 Hz, 6H, H-30 and H-31); 0.96 (d, J=7 Hz, 3H, H-21); 3.06 (dd, J=8.5, 7.5 Hz, 1H, H-22); 3.34 (m, 3H, H-22′ and H-24); 4.13 (m, 1H, H-3); 4.30 (m, 1H, H-1); 4.80 and 5.12 (s; 1H, H-19 each); 5.96 and 6.18 (d, J=11 Hz; 1H, H-6 and H-7 each) [α]$_D^{20}$: +36.8°, c=0.22; CHCl$_3$

24-(1-Hydroxy-1-propylbutyl)-23-oxa-9,10-seco-5(Z),7(E),10(19)-cholatriene-1α,3β-diol 6b 120 mg of 5b is reacted with 1.2 ml of tetrabutylammonium fluoride solution (1M in THF) analogous to 6a. 47 mg of the title compound is obtained as colorless foam.

$^1$H-NMR (CDCl$_3$): δ=0.57 ppm (s, 3H, H-18); 0.91 (t, J=7 Hz, 6H, H-30 and H-31); 1.04 (d, J=7 Hz, 3H, H-21); 3.14 (dd, J=10, 6 Hz, 1H, H-22); 3.18 (d, J=9 Hz, 1H, H-24); 3.26 (d, J=9 Hz, 1H, H-24′); 3.40 (dd, J=10, 4 Hz, 1H, H-22′); 4.24 (m, 1H, H-3); 4.44 (m, 1H, H-1); 5.00 and 5.33 (s; 1H, H-19 each); 6.03 and 6.38 (d, J=11 Hz; 1H, H-6 and H-7 each) [α]$_D^{20}$: +22.2°, c=0.175; CHCl$_3$

1α,3β-Bis[[dimethyl(1,1-dimethylethyl)silyl]oxy]-24-(1-hydroxy-1-methylethyl)-23-oxa-9,10-seco-5(E),7(E),10(19)-cholatriene 4c 820 mg of 3 is reacted with the Grignard reagent made of 290 mg of magnesium chips and 0.74 ml of methyl iodide in 13 ml of diethyl ether analogous to 4a. 360 mg of the title compound is obtained as colorless foam.

$^1$H-NMR (CDCl$_3$): δ=0.01 ppm (s, 12H, Si—CH$_3$); 0.50 (s, 3H, H-18); 0.81 and 0.83 (s; 9H, Si-t-butyl each); 1.00 (d, J=7 Hz, 3H, H-21); 1.16 (s, 6H, H-26 and H-27); 3.11 (d, J=9.5 Hz, 1H, H-24); 3.16 (m, 1H, H-22); 3.21 (d, J=9.5 Hz, 1H, H-24′); 3.48 (dd, J=9.4 Hz, 1H, H-22′); 4.18 (m, 1H, H-3); 4.48 (m, 1H, H-1); 4.89 and 4.94 (s; 1H, H-19 each); 5.78 and 6.40 (d, J=11 Hz; 1H, H-6 and H-7 each) [α]$_D^{20}$: +51.2°, c=0.505; CHCl$_3$

1α,3β-Bis[[dimethyl(1,1-dimethylethyl)silyl]oxy]-24-(1-hydroxy-1-methylethyl)-23-oxa-9,10-seco-5(Z),7(E),10(19)-cholatriene 5c 330 mg of 4c is reacted with 50 mg of anthracene and 15 μl of triethylamine in 80 ml of toluene analogous to 5a, and 280 mg of the title compound is obtained as colorless foam.

$^1$H-NMR (CDCl$_3$): δ=0.01 ppm (s, 12H, Si—CH$_3$); 0.49 (s, 3H, H-18); 0.82 (s, 18H, Si-t-butyl); 0.99 (d, J=7 Hz, 3H, H-21); 1.15 (s, 6H, H-26 and H-27); 3.11 (d, J=9.5 Hz, 1H, H-24); 3.17 (m, 1H, H-22); 3.20 (d, J=9.5 Hz, 1H, H-24′); 3.38 (dd, J=9.4 Hz, 1H, H-22′); 4.14 (m, 1H, H-3); 4.31 (m, 1H, H-1); 4.81 and 5.12 (s; 1H, H-19 each); 5.96 and 6.19 (d, J=11 Hz; 1H, H-6 and H-7 each) [α]$_D^{20}$: +46.6°, c=0.12; CHCl$_3$

24-(1-Hydroxy-1-methylethyl)-23-oxa-9,10-seco-5(Z),7(E),10(19)-cholatriene-1α,3β-diol 6c 260 mg of 5c is reacted with 1.6 ml of tetrabutylammonium fluoride solution (1M in THF) analogous to 6a. 117 mg of the title compound is obtained as colorless foam.

$^1$H-NMR (CDCl$_3$): δ=0.56 ppm (s, 3H, H-18); 1.04 (d, J=7 Hz, 3H, H-21); 1.22 (s, 6H, H-26 and H-27); 3.16 (d, J=9 Hz, 1H, H-24); 3.22 (m, 1H, H-22); 3.26 (d, J=9 Hz, 1H, H-24′); 3.43 (dd, J=9, 4.5 Hz, 1H, H-22′); 4.22 (m, 1H, H-3); 4.43 (m, 1H, H-1); 5.01 and 5.33 (s; 1H, H-19 each); 6.03 and 6.39 (d, J=11 Hz; 1H, H-6 and H-7 each) [α]$_D^{20}$: +22°; c=0.15; CHCl$_3$

3-[1α,3α-Bis[[dimethyl(1,1-dimethylethyl)silyl]oxy]-23-oxa-9,10-seco-5(E),7(E),10(19)-cholatrien-24-yl]-propionic acid methyl ester 7

2.3 g of 2 is stirred overnight at room temperature with 3.75 g of bromobutyric acid-orthotrimethyl ester and 212 mg of tetrabutylammonium hydrogen sulfate in 5.4 ml of sodium hydroxide solution (50%). It is diluted with water, extracted with ethyl acetate, washed with sodium chloride solution, dried on sodium sulfate and concentrated by evaporation. The residue is chromatographed on silica gel with hexane/ethyl acetate and 1.42 g of the title compound accumulates.

$^1$H-NMR (CDCl$_3$): δ=0.01 ppm (s, 12H, Si—CH$_3$); 0.50 (s, 3H, H-18); 0.80 and 0.82 (s; 9H, Si-t-butyl each); 0.96 (d, J=7 Hz, 3H, H-21); 2.11 (q, J=7 Hz, 2H, H-25); 2.36 (t, J=7 Hz, 2H, H-26); 3.32 (m, 2H, H-22); 3.40 (t, J=7 Hz, 2H, H-24); 3.61 (s, 3H, methylester); 4.17 (m, 1H, H-3); 4.48 (m, 1H, H-1); 4.88 and 4.93 (s; 1H, H-19 each); 5.76 and 6.40 (d, J=11 Hz; 1H, H-6 and H-7 each) [α]$_D^{20}$: +52.7°, c=0.4; CHCl$_3$

1α,3β-Bis[[dimethyl(1,1-dimethylethyl)silyl]oxy]-24-(3-hydroxy-3methylbutyl)-23-oxa-9,10-seco-5(E),-7(E),10(19)-cholatriene 8a The Grignard reagent made from 253 mg of magnesium chips and 0.65 ml of methyl iodide in 13 ml of diethyl ether is reacted with 700 mg of 7 analogous to 4a. 380 mg of the title compound is obtained as colorless foam.

$^1$H-NMR (CHCl$_3$): δ=0.08 ppm (s, 12H, Si—CH$_3$); 0.55 (s, 3H, C18); 0.89 (s, 18H, Si-t-butyl); 1.04 (d, J=7 Hz, 3H, H-21); 1.22 (s, 6H, H-28 and H-29); 3.13 and 3.43 (m, 4H, H-22 and H-24); 4.22 (m, 1H, H-3); 4.54 (m, 1H, H-1); 4.96 and 5.00 (s; 1H, H-19 each); 5.83 and 6.46 (d; 1H, H-6 and H-7 each) [α]$_D^{20}$: +28.1°, c=0.515; CHCl$_3$

1α,3β-Bis[[dimethyl(1,1-dimethylethyl)silyl]oxy]-24-(3-hydroxy-3methylbutyl)-23-oxa-9,10-seco-5(Z),7(E),10(19)-cholatriene 9a 370 mg of 8a is reacted with 88 mg of anthracene and 20 μl of triethylamine in 80 ml of toluene analogous to 5a. 221 mg of the title compound is obtained as colorless foam.

¹H-NMR (CDCl₃): δ=0.01 ppm (s, 12H, Si—CH₃); 0.48 (s, 3H, H-18); 0.80 (s, 18H, Si-t-butyl); 0.98 (d, J=7 Hz, 3H, H-21); 1.16 (s, 6H, H-28 and H-29); 3.06 (dd, J=8.5, 7.5 Hz, 1H, H-22); 3.35 (m, 3H, H-22' and H-24); 4.13 (m, 1H, H-1); 4.31 (m, 1H, H-1); 4.80 and 5.11 (s; 1H, H-19 each); 5.96 and 6.17 (d, J=11 Hz; 1H, H-6 and H-7 each) [α]$_D^{20}$: +24°, c=0.345; CHCl₃

24-(3-Hydroxy-3-methylbutyl)-23-oxa-9,10-seco-5(Z),7(E),10(19)-cholatriene-1α,3β-diol 10a 200 mg of 9a is reacted with 1.13 ml of tetrabutylammonium fluoride solution (1M in THF) analogous to 6a. 113 mg of the title compound is obtained.

¹H-NMR (CDCl₃): δ=0.55 ppm (s, 3H, H-18); 1.03 (d, J=7 Hz, H-21); 1.20 (s, 6H, H-28 and H-29); 3.12 (dd, J=8.5, 7.5 Hz, 1H, H-22); 3.39 (m, 3H, H-22' and H-24); 4.22 (m, 1H, H-3); 4.43 (m, 1H, H-1); 5.00 and 5.32 (s; 1H, H-19 each); 6.02 and 6.38 (d, J=11 Hz; 1H, H-6 and H-7 each) [α]$_D^{20}$: +20.9°, c=0.415; CHCl₃

1α,3β-Bis[[dimethyl(1,1-dimethylethyl)silyl]oxy]-24-(3-ethyl-3hydroxypentyl)-23-oxa-9,10-seco-5(E),-7(E),10(19)-cholatriene 8b 700 mg of 7 is reacted with the Grignard reagent made from 253 mg of magnesium chips and 0.78 ml of bromoethane in 13 ml of THF analogous to 4a. 360 mg of the title compound is obtained as colorless foam.

¹H-NMR (CDCl₃): δ=0.01 ppm (s, 12H, Si—CH₃); 0.50 (s, H, H-18); 0.80 and 0.85 (s; 9H, Si-t-butyl each); 0.81 and 0.83 (t, J=7 Hz; 3H, H-30 and H-31 each); 0.99 (d, J=7 Hz, H-21); 3.08 (dd, J=9, 7.5 Hz, 1H, H-22); 3.35 (m, 3H, H-22' and H-24); 4.18 (m, 1H, H-3); 4.49 (m, 1H, H-i); 4.88 and 4.94 (s; 1H, H-19 each); 5.78 and 6.40 (d, J=11 Hz; 1H, H-6 and H-7 each) [α]$_D^{20}$: +55.2°, c=0.46; CHCl₃

1α,3β-Bis[[dimethyl(1,1-dimethylethyl)silyl]oxy]-24-(3-ethyl-3-hydroxypentyl)-23-oxa-9,10-seco-5(Z),7(E),10(19)-cholatriene 9b 350 mg of 8b is reacted with 80 mg of anthracene and 18 μl of triethylamine analogous to 5b. 300 mg of the title compound is obtained as colorless foam.

1H-NMR (CDCl₃): δ=0.01 ppm (s, 12H, Si—CH₃); 0.49 (s, 3H, H-18); 0.80 (s, 18H, Si-t-butyl); 0.80 (t, J=7 Hz, 6H, H-30 and H-31); 0.96 (d, J=7 Hz, 3H, H-21); 3.06 (dd, J=8.5, 7.5 Hz, 1H, H-22); 3.34 (m, 3H, H-22' and H-24); 4.13 (m, 1H, H-3); 4.30 (m, 1H, H-1); 4.80 and 5.12 (s; 1H, H-19 each); 5.96 and 6.18 (d, J=11 Hz; 1H, H-6 and H-7 each) [α]$_D^{20}$: +38.6°, c=0.22 CHCl₃

24-(3-Ethyl-3-hydroxypentyl1)-23-oxa-9,10-seco-5(Z),7(E),10(19)-cholatriene-1α,3β-diol 10b 290 mg of 9b is reacted with 1.54 ml of tetrabutylammonium fluoride solution (1M in THF) analogous to 6b. 106 mg of the title compound is obtained as colorless foam.

¹H-NMR (CDCl₃): δ=0.55 ppm (s, 3H, H-18); 0.84 (t, J=7 Hz, 6H, H-30 and H-31); 1.07 (d, J=7 Hz, 3H, H-21); 1.48 (q, J=7 Hz, 4H, H-28 and H-29); 3.12 (dd, J=8.5, 7.5 Hz, 1H, H-22); 3.40 (m, 3H, H-22' and H-24); 4.22 (m, 1H, H-3); 4.43 (m, 1H, H-1); 5.00 and 5.33 (s; 1H, H-19 each); 6.03 and 6.38 (d, J=11 Hz; 1H, H-6 and H-7 each) [α]$_D^{20}$: +18.4°, c=0.13 CHCl₃

1α,3β-Bis[[dimethyl(1,1-dimethylethyl)silyl]oxy]-24-(1-ethyl-hydroxy-propyl)-23-oxa-9,10-seco-5(E),-7(E),10(19)-cholatriene 4a Test of the preparation analogous to Hesse U.S. Pat. No. 4,772,433 or EP 0078704

410 mg of 2 is refluxed 55 minutes with 1.4 g of 1,2-epoxy-2-ethylbutane [preparation analogous to J. S. Ng Synthetic Communications 20, 1193 (1990)], 50 mg of dibenzo-18-crown-6 and 252 mg of potassium-tert.-butanolate in 5 ml of benzene. It is diluted with water, extracted with methylene chloride, washed with sodium bicarbonate solution and sodium chloride solution and dried on sodium sulfate. After removal of the solvent the residue is purified on silica gel with hexane/ethyl acetate and 30 mg of the initial material accumulates as sole characterizable product.

We claim:

1. 23-Oxa-derivatives in the vitamin D series of formula I

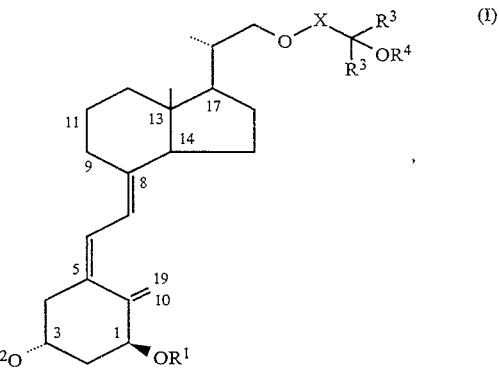

in which

R¹, R² and R⁴ independently of one another mean a hydrogen atom or an acyl group with 1 to 9 carbon atoms, each R³ is a hydrogen atom or each R³ is a linear or branched alkyl group with 1 to 4 carbon atoms and X means an alkylene radical—(CH₂)$_n$— wherein n is 1, 2 or 3 and if n=1, R³ cannot be a methyl group.

2. 24-(1-ethyl-1-hydroxypropyl)-23-oxa-9,10-seco-5(Z),7(E),10(19)-cholatriene-1α,3β-diol, 24-(1-hydroxy-1-propylbutyl)-23-oxa-9,10-seco-5(Z),7(E),10(19)-cholatriene-1α,3β-diol, 24-(3-hydroxy-3-methylbutyl)-23-oxa-9,10-seco-5(Z),7(E),10(19)-cholatriene-1α,3β-diol, 24-(3-ethyl-3 -hydroxypentyl)-23-oxa-9,10-seco-5(Z),7(E),10(19)-cholatriene-1α,3β-diol each a compound of claim 1.

3. Process for the production of compounds of general formula I'

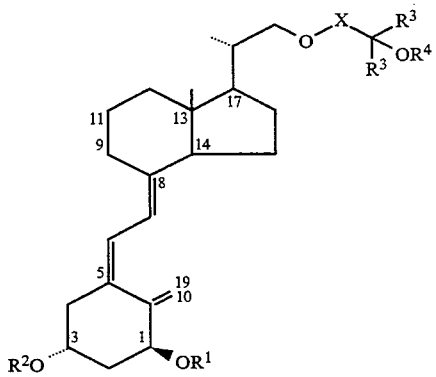

(I')

in which

R$^1$, R$^2$ and R$^4$ independently of one another mean a hydrogen atom or an acyl group with 1 to 9 carbon atoms, each R$^3$ is a hydrogen atom or each R$^3$ is a linear or branched alkyl group with 1 to 4 carbon atoms and X means an alkylene radical —(CH$_2$)$_n$— wherein n is 1, 2 or 3 characterized in that a compound of general formula II

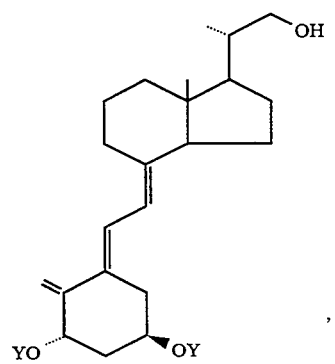

(II)

in which Y means alkyl or aryl substituted silyl groups is etherified, with a compound of general formula III

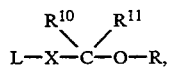

(III)

in which

L stands for a leaving group selected from the group consisting of Br, I and CH$_3$—C$_6$H$_4$SO$_2$O—, X stands for an alkylene radical —(CH$_2$)$_n$— wherein n is 1, 2 or 3, R stands for a straight-chain or branched alkyl radical with 1 to 8 carbon atoms, R$^{10}$ and R$^{11}$ each stand for a radical OR or R$^{10}$ and R$^{11}$ together stand for an oxygen atom thus obtaining a compound of general formula IV

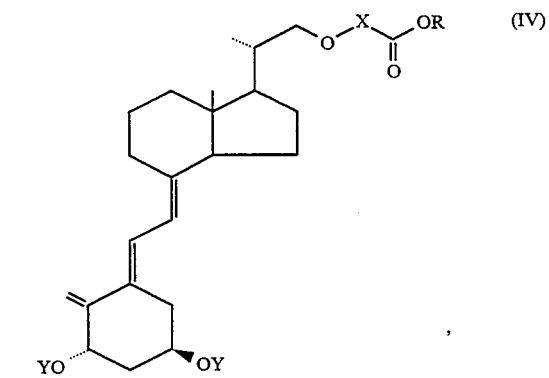

(IV)

on whose carbonyl group a nucleophilic reagent of general formula V

R$^3$—Z (V)

is added in which R$^3$ means a linear or branched alkyl group with 1 to 4 carbon atoms where Z is MgHal where Hal is selected from Cl, Br, and I or is an alkali atom selected from Li, Na, and K or if R$^3$ is a hydrogen atom, R$^3$—Z is a complex hydride, with the formation of a compound of general formula VI

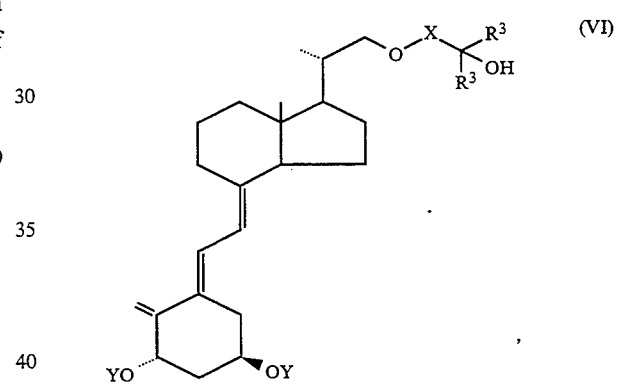

(VI)

and the latter is converted by photochemical isomerization of the triene system in the presence of a triplet sensitizer into a compound of general formula VII

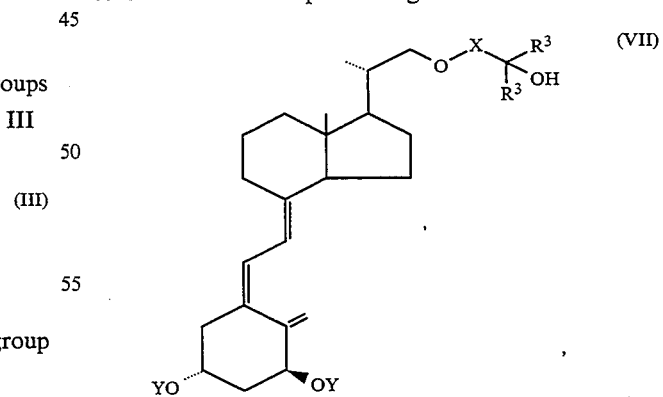

(VII)

and the silyl protective groups are cleaved off and then optionally the free hydroxy groups are partially or completely esterified with a carboxylic acid chloride or anhydride, which have 1 to 9 carbon atoms in the acyl radical.

4. Pharmaceutical preparation comprising at least one compound of claim 1 and a pharmaceutically compatible vehicle.

5. A method as in claim 3, wherein R$_3$—Z is the complex hydride lithium aluminum hydride.

* * * * *